United States Patent
Suda et al.

(10) Patent No.: US 8,163,556 B2
(45) Date of Patent: Apr. 24, 2012

(54) METHOD OF CELL CULTURE OBSERVATION, CARBON SUBSTRATE FOR CELL CULTURE OBSERVATION, AND METHOD FOR MANUFACTURE THEREOF

(75) Inventors: Yoshihisa Suda, Gunma (JP); Kunitaka Yamada, Gunma (JP); Hiroko Kaneko, Ibaraki (JP); Kaoru Katoh, Ibaraki (JP); Harumasa Okamoto, Ibaraki (JP)

(73) Assignees: Mitsubishi Pencil Co., Ltd., Tokyo (JP); Kaora Katoh, Ibaraki (JP); Hiroko Kaneko, Ibaraki (JP)

( * ) Notice: Subject to any disclaimer, the term of this patent is extended or adjusted under 35 U.S.C. 154(b) by 0 days.

(21) Appl. No.: 11/276,263

(22) Filed: Feb. 21, 2006

(65) Prior Publication Data

US 2006/0194312 A1    Aug. 31, 2006

(30) Foreign Application Priority Data

Feb. 21, 2005  (JP) .................................. 2005-43605

(51) Int. Cl.
- C01B 31/00 (2006.01)
- B32B 5/02 (2006.01)
- B32B 27/04 (2006.01)
- G01N 21/00 (2006.01)
- C12N 5/00 (2006.01)

(52) U.S. Cl. ....... 435/395; 422/50; 422/82.05; 435/325; 435/368; 435/396; 435/402; 436/43; 436/164; 264/29.1

(58) Field of Classification Search .................. 435/395, 435/325, 368; 422/50, 82.05; 264/29.1; 436/43, 164

See application file for complete search history.

(56) References Cited

U.S. PATENT DOCUMENTS 4,968,623 A * 11/1990 Franks ........................ 435/304.3
2001/0036665 A1* 11/2001 Young et al. .................. 435/374

FOREIGN PATENT DOCUMENTS

| JP | 06-070755 A | 3/1994 |
|---|---|---|
| JP | 2002-335945 A | 11/2002 |
| JP | 2002365293 | * 12/2002 |
| JP | 2003-009860 A | 1/2003 |
| JP | 2004-049176 A | 2/2004 |
| JP | 2004-135668 A | 5/2004 |

OTHER PUBLICATIONS

De Laurenzi V, et al., Induction of neuronal differentiation by p73 in a neuroblastoma cell line. J Biol Chem. May 19, 2000;275(20):15226-31.*
Tokai Carbon USA—Glassy Carbon Store—Copyright © 2009 Tokai Carbon USA. www.glassycarbonstore.com/contact_us.html.*
Marsh, H. and Rodriguez-Reinoso, F, Activated Carbon (Elsevier, 2006) pp. 15,17, 101, 110,111, 112, 270, 473, 482, 486 and 487.*
Schmalenberg et al., Biomaterials, 2005 Micropatterned polymer substrates control alignment of proliferating Schwann cells to direct neuronal regenertion pp. 1423-1430.*
Sia et al., Microfluidic devices fabricated in poly (dimethylsiloxane) for biological studies Electrophoresis, 2003 pp. 3563-3576.*
Kim et al., Structural and Property Changes in Glass-like Carbons Formed by Heat Treatment and Addition of Filler; 2004, Macromolecular Research pp. 399-406.*
Fink et al., Reactive Polymers Fundamentals and Applications pp. 307-320. 2005.*
Office Action mailed Jul. 5, 2011, in corresponding Japanese Patent Application 2005-043605, with English translation, 7 pages.
Office Action mailed Dec. 21, 2010, in corresponding Japanese Patent Application 2005-43605. with English translation, 10 pages.
Dorner-Reisel et al., "Diamond-like carbon: alteration of the biological acceptance due to Ca-O incorporation," Thin Solid Films, 2002, 420-421:263-268.

* cited by examiner

*Primary Examiner* — Maria Leavitt
(74) *Attorney, Agent, or Firm* — Foley & Lardner LLP

(57) ABSTRACT

The invention provides a substrate suitable for cell culture observation and a method of observation using the same. Crystalline carbon such as a graphite powder is mixed into a thermosetting resin such as a furan resin, and the mixture is molded in the shape of a sheet and carbonized to produce a carbon substrate; then, a cell is made to adhere to the carbon substrate, and the cell is caused to proliferate on the carbon substrate and observed using a microscope.

8 Claims, 8 Drawing Sheets

METHOD OF CELL CULTURE OBSERVATION, CARBON SUBSTRATE FOR CELL CULTURE OBSERVATION, AND METHOD FOR MANUFACTURE THEREOF

BACKGROUND OF THE INVENTION

1. Field of the Invention

The present invention relates to a method for observing a cell under a microscope by causing the cell to proliferate, a substrate used for the same, and a method for the manufacture thereof.

2. Description of the Related Art

Unlike bacteria, most animal cells cannot divide or proliferate in suspension; therefore, such cells are cultured by being attached to a surface of a suitable object. In this case, the cell culture is often performed by attaching the cells to thin glass (cover glass or slide glass) or plastic whose surface is treated so that the cells can easily adhere to it. In order to know the distribution of specific protein molecules within the cells in culture, it is widely practiced to mark the protein under study with fluorescence and to observe the distribution of the specific protein molecules by using a reflected light fluorescence microscope or a confocal microscope.

In this fluorescence microscope observation, it is desired to reduce the fluorescence and reflection of any substance on the background other than the cells. Today, glass with reduced fluorescence is used, but the fluorescence and reflection of the glass itself exist to such a degree that they are still explicitly detectable.

As described above, for cell proliferation, the cells must be made to adhere to the surface of a substrate. For this purpose, it is practiced to coat the substrate (for example, the inner bottom surface of a glass or plastic cell culture dish) with a suitable substance (poly-L lysine or collagen or the like) or chemically modify it with a certain kind of residue (for example, an amino group) so that the cells can easily adhere to it. As is generally recognized, a substrate for biological specimen observation must have a surface to which cells can easily adhere, or must have surface treatable to provide such a surface.

SUMMARY OF THE INVENTION

Accordingly, it is an object of the present invention to provide a substrate suitable for cell culture observation and a method of observation using the same.

According to the present invention, there is provided a method of cell culture observation, comprising: making a cell adhere onto a carbon substrate; causing the cell to proliferate on the carbon substrate; and observing the cell under a microscope.

According to the present invention, there is also provided a carbon substrate for cell culture observation, which contains a glass-like carbon obtained by baking a resin, and on a surface of which a cell is caused to proliferate and observed under a microscope.

Preferably, the carbon substrate contains crystalline carbon dispersed uniformly through the glass-like carbon, in proportions not smaller than 1% by mass but not larger than 40% by mass.

The crystalline carbon is at least one material selected from the group consisting, for example, of carbon nanotubes, graphite whiskers, highly oriented pyrolytic graphite, kish graphite, natural graphite, artificial graphite, fullerene, and graphite fiber chop.

The carbon substrate is manufactured by mixing crystalline carbon in a liquid composition of a thermosetting resin, molding the mixture into a desired substrate shape while performing control so that the graphite is uniformly dispersed therein, and then baking the molding in an inert atmosphere or a non-oxidizing atmosphere or in a vacuum.

The carbon substrate for cell culture observation according to the present invention has excellent characteristics for use as the carbon substrate for cell culture observation, because the substrate is non-fluorescent and hardly reflective and provides, without any specific surface treatment, a surface on which cells can adhere and be cultured.

Further, by mixing crystalline carbon such as graphite or carbon nanotube before baking the resin, composite carbon with the crystalline carbon uniformly dispersed in glass-like carbon can be obtained.

The composite carbon material obtained by uniformly dispersing the crystalline carbon through the glass-like carbon as described above serves to enhance cell adsorbing ability because of the presence of crystal edges exposed in the surface; further, as its processability also improves, the surface can be made flat enough not to cause a problem in microscope observation.

EXAMPLES

Figure 1:
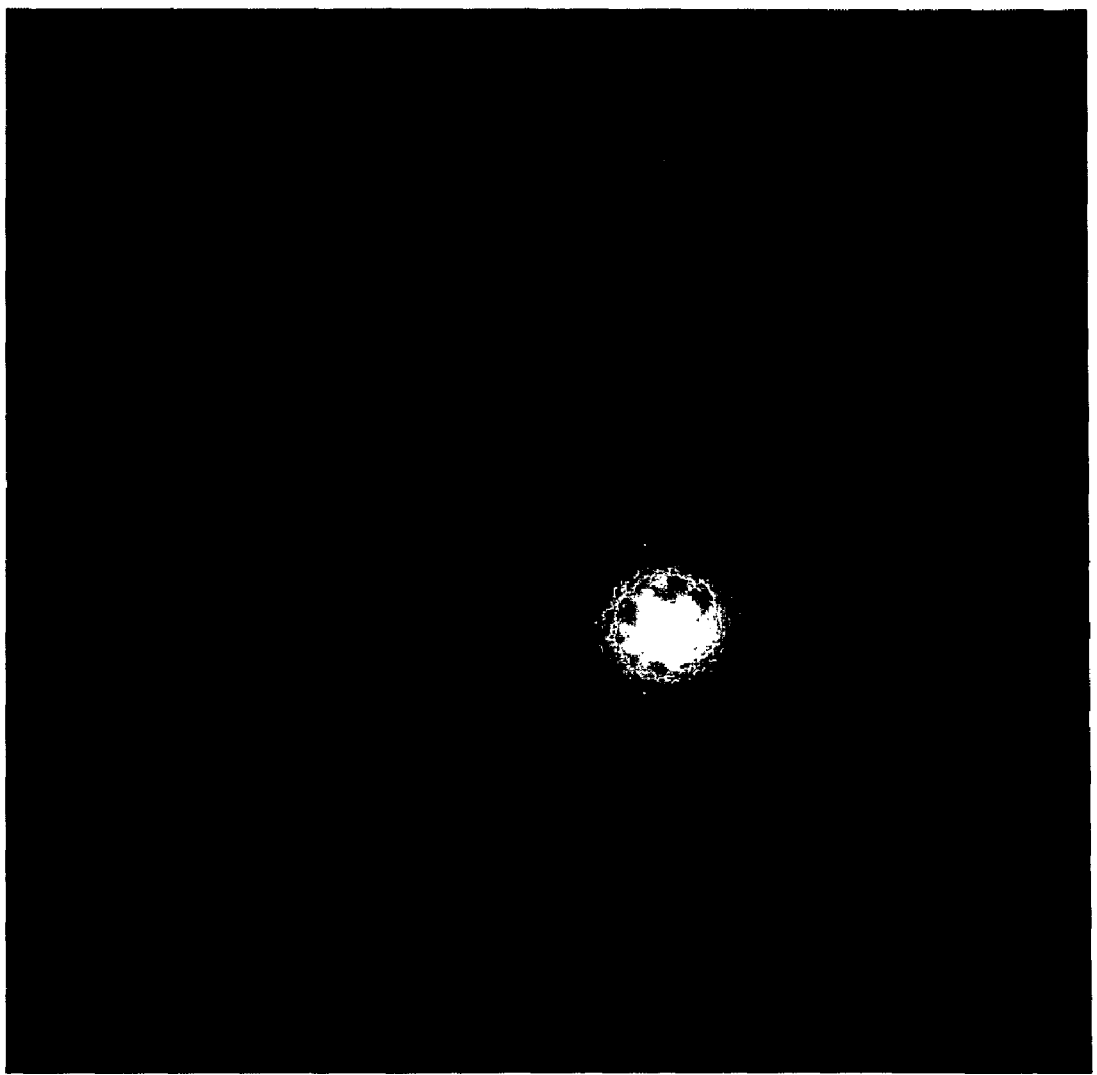
FIG. 1 is a diagram showing an image of a cell cultivated on a carbon substrate.

Eight parts of natural crystalline graphite powder (with an average particle size of 1 µm, manufactured by Nippon Graphite) were added to 92 parts of furan resin (HITAFURAN VF-302 manufactured by Hitachi Chemical), and were thoroughly dispersed and mixed therein to prepare a liquid material for a substrate. Next, the liquid material was charged into a doctor-blade-type coating machine, and a green sheet was formed by setting the material after coating. The green sheet was then formed into a disk shape, and the thus formed sheet was heated and cured in a drying furnace to obtain a cured plate. The cured plate was then carbonized in a nitrogen gas atmosphere by raising the temperature up to 1000° C. in 50 hours, after which the plate was treated at 1400° C. in a high-temperature vacuum furnace, to obtain a disk-shaped, totally carbonaceous substrate composed of glass-like carbon and graphite in proportions of about 80:20 in terms of mass ratio and having a diameter of 35 mm and a Shore hardness of 90. The thus obtained substrate was ground to a thickness of 1.0 mm by a surface grinder (using a vacuum chuck) to produce a substrate for cell culture observation.

The cell lines used for cell culture were neuroblastoma cells (NG108) and epithelial cells (NIH3T3) purchased from The American Type Culture Collection (ATCC). The culture solution used was Dulbecco's Modified Eagle Medium. Plasmids containing the green florescent protein (GFP) gene (purchased from Clontech) were introduced into the cell lines by a lipofection method using a gene injection kit manufactured by Qiagen.

The 35-mm diameter disk-shaped carbon substrate was placed on the bottom surface of one of two plastic dishes (each with a 35-mm inner diameter) sterilized with γ-ray radiation, and a cover glass (24 mm square, manufactured by Matsunami Glass) treated with a cell proliferation coating (poly-L lysine coating) was placed in the other plastic dish, and UV sterilization was performed for 30 minutes. Then, the culture solution was put therein, and the solution containing the cells with the gene introduced therein was added, the cell density being adjusted to $1 \times 10^4$ cells/ml. The culture dishes were placed and left in a carbon dioxide incubator (37 degrees with the $CO_2$ density controlled to 5%).

The cells quickly adhered to the carbon substrate and divided and proliferated; after a few days, about 7 to 80% of the cells expressed the green fluorescent protein gene, thus transforming into cells illuminating in green. In the case of the non-treated carbon substrate, the cells proliferated just as they did on the cover glass treated with the cell proliferation coating.

The plastic culture dish, on the bottom surface of which the slide glass or the carbon substrate with the cells proliferated thereon was sitting, was held fixed onto the stage of an upright optical microscope (Olympus AX-70) and, by immersing the tip of an immersion objective lens (magnification 60×) in the culture solution, the fluorescence (green) of living cells was observed by using the reflected light fluorescence device of the microscope. The images of the cells dyed green with the fluorescence were recorded by using a cooled CCD camera.

Figure 2:
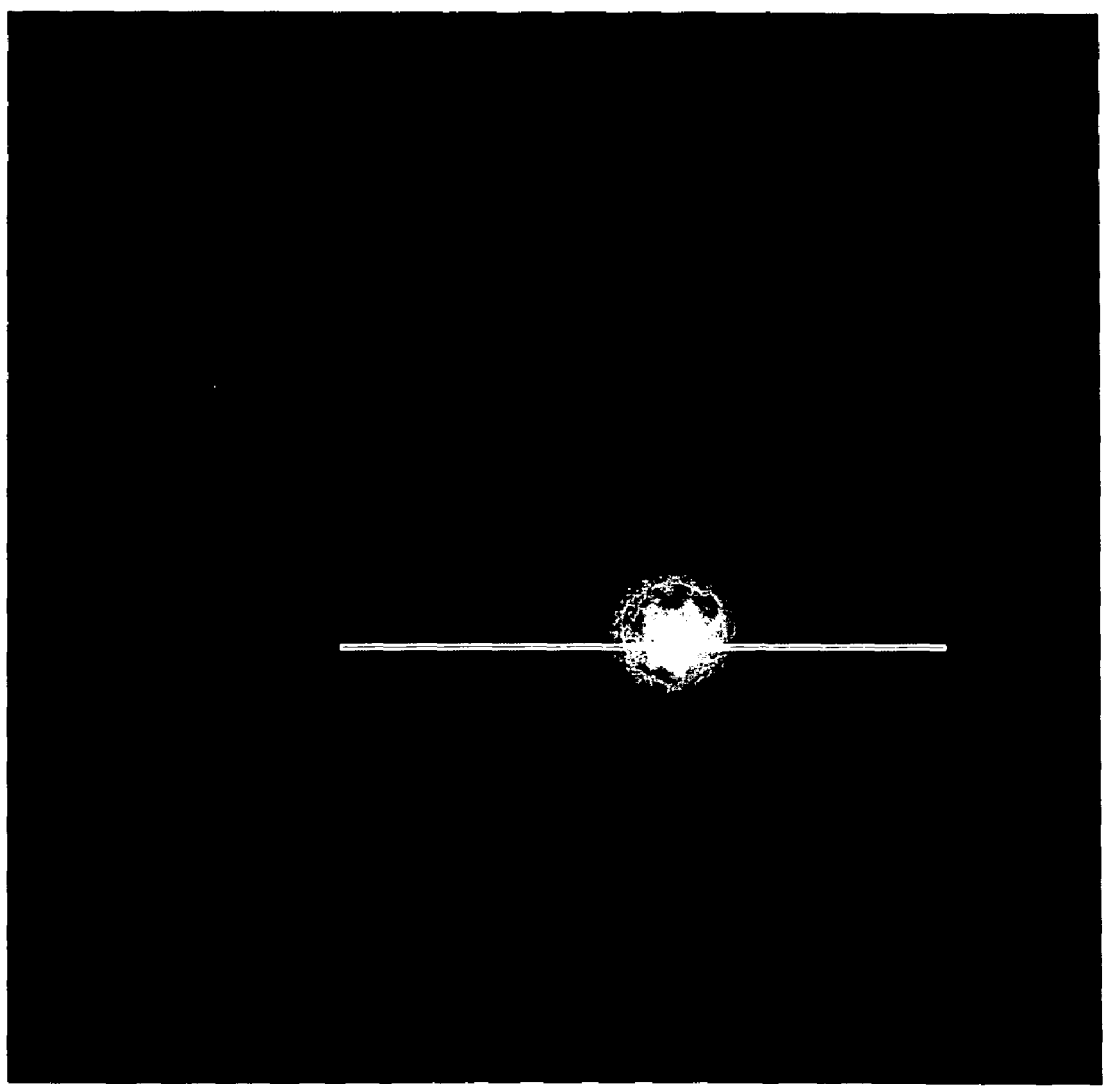
FIG. 2 is a diagram showing an image produced by putting in the image of FIG. 1 a white line indicating the position of a plot profile.
Figure 3:
FIG. 3 is a graph showing luminance values on the white line.
Figure 4:
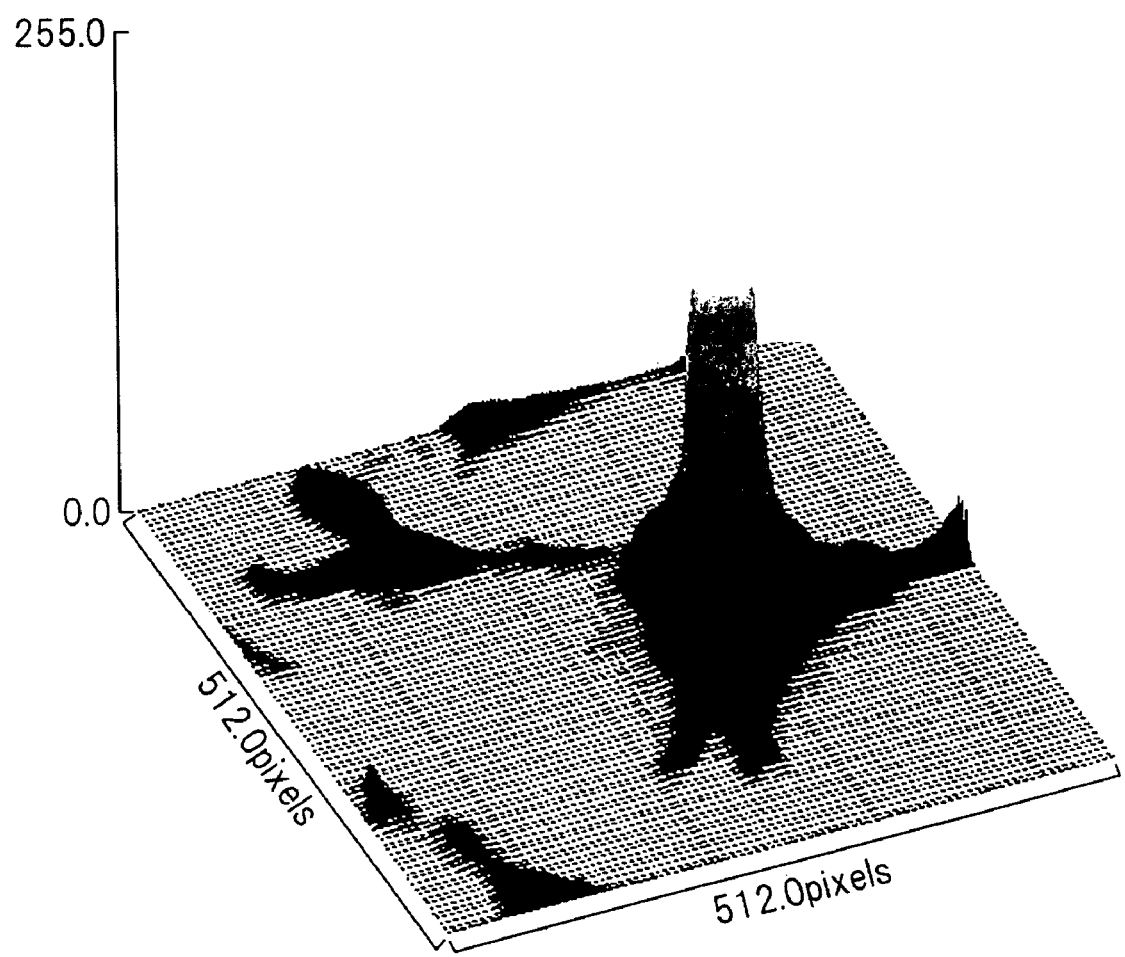
FIG. 4 is a diagram showing the distribution of luminance values across the image of FIG. 1 by using contour lines.
Figure 5:
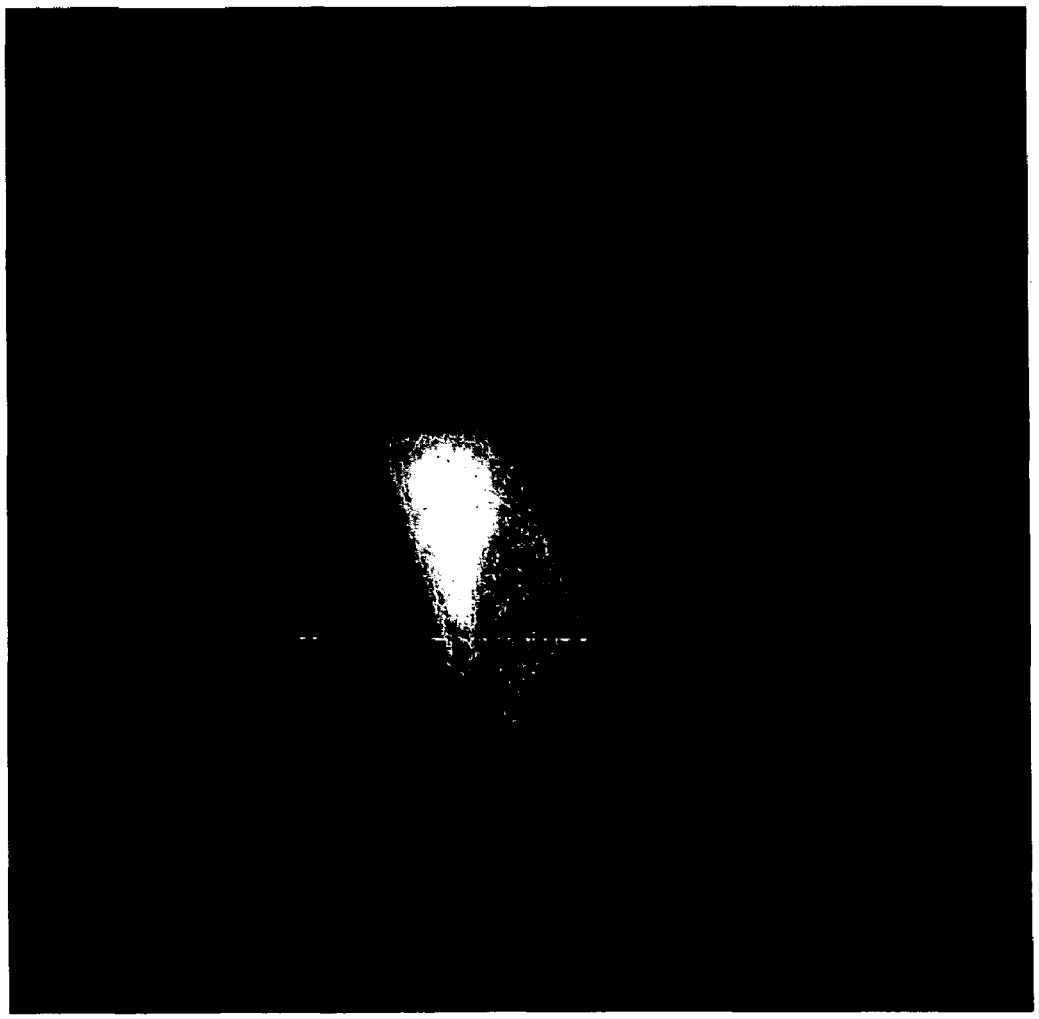
FIG. 5 is a diagram showing an image of a cell cultivated on a glass substrate.
Figure 6:
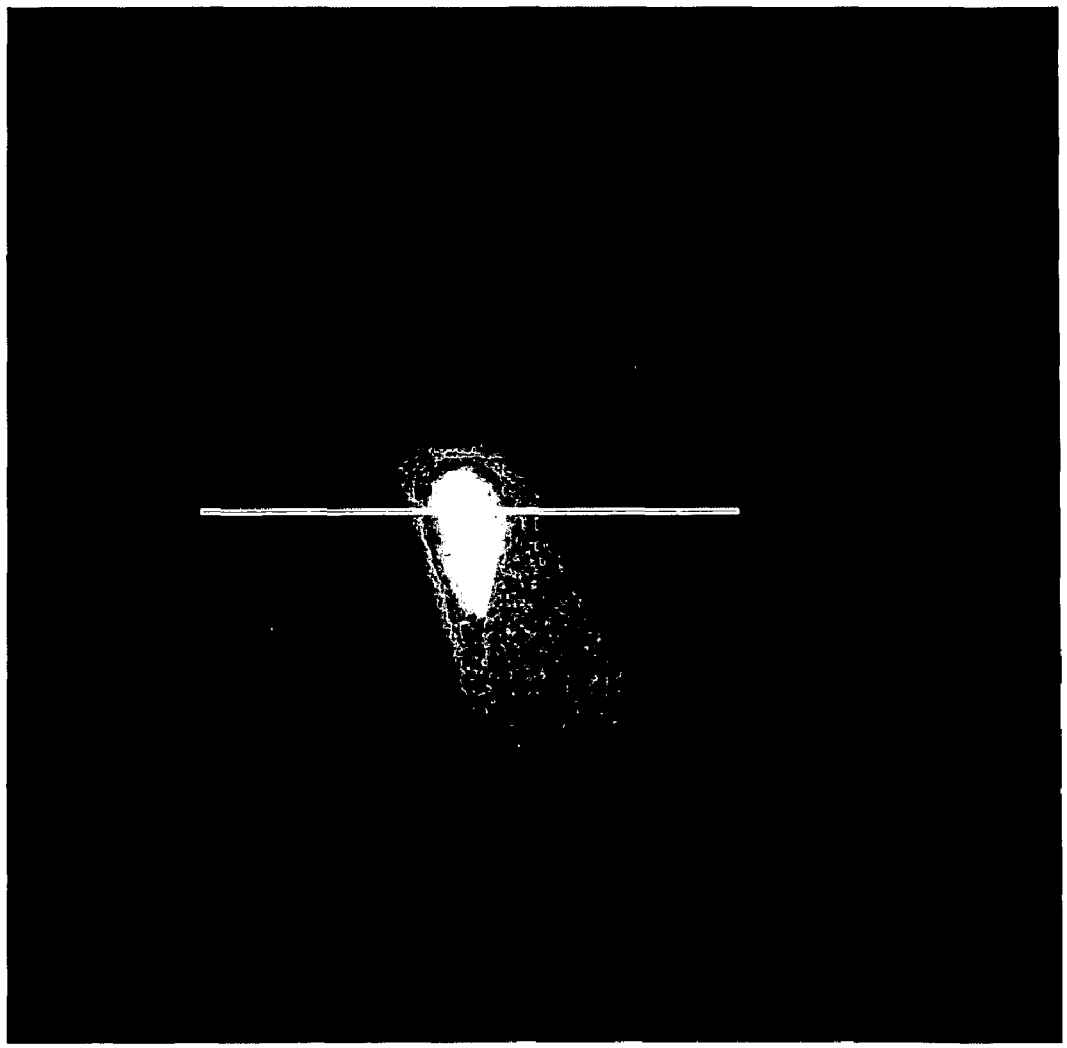
FIG. 6 is a diagram showing an image produced by putting in the image of FIG. 5 a white line indicating the position of a plot profile.
Figure 7:
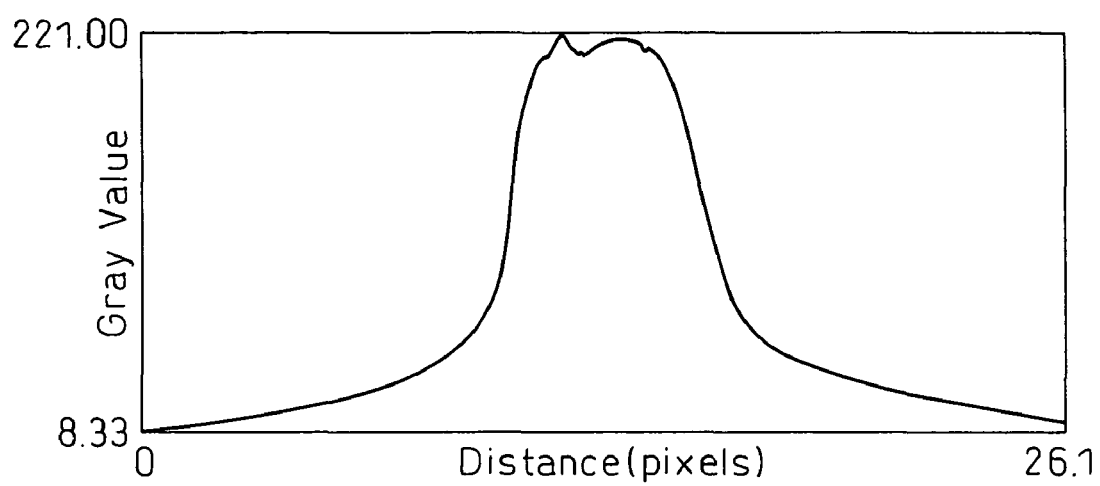
FIG. 7 is a graph showing luminance values on the white line.
Figure 8:
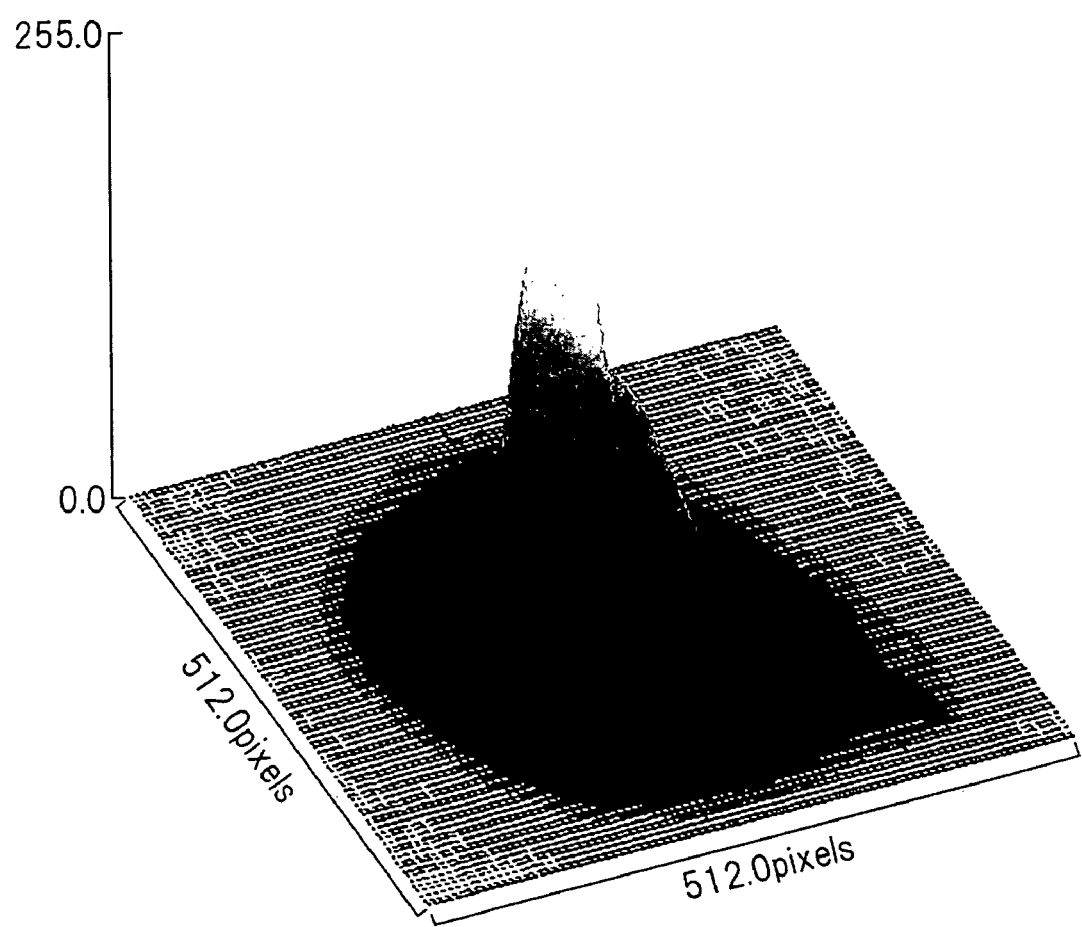
FIG. 8 is a diagram showing the distribution of luminance values across the image of FIG. 5 using contour lines.

FIG. 1 shows an image of a cell cultivated on the carbon substrate, FIG. 2 shows an image produced by putting in the image of FIG. 1 a white line indicating the position of a plot profile, FIG. 3 is a graph showing luminance values on the white line, and FIG. 4 is a diagram showing the distribution of luminance values across the image of FIG. 1 by using contour lines. Further, FIG. 5 shows an image of a cell cultivated on the glass substrate, FIG. 6 shows an image produced by putting in the image of FIG. 5 a white line indicating the position of a plot profile, FIG. 7 is a graph showing luminance values on the white line, and FIG. 8 is a diagram showing the distribution of luminance values across the image of FIG. 5 by using contour lines.

As is apparent from a comparison between FIGS. 1 to 4 and FIGS. 5 to 8, a higher-contrast, clearer image was obtained for the cell cultivated on the carbon substrate because the reflection and fluorescence on the background were reduced.

It is known that a neuron extends its axon along a substance having an affinity for a nerve (for example, an extracellular matrix protein such as fibronectin, laminin, or collagen). If such a substance is applied in a prescribed pattern on the surface of the carbon substrate, it is possible to create a neural circuit by allowing the neuron to extend along the pattern. By making provisions so that the fluorescent protein is expressed inside the neuron, the neuron in the process of extending along the substance can be observed using a reflected light fluorescence microscope or a confocal microscope. A similar effect can be obtained if a polyamino acid such as poly-L lysine, poly-D lysine, or poly-D ornithine, or concanavalin A or the like is used instead of the above extracellular matrix protein.

The invention claimed is:

1. A method of cell culture observation, comprising:
   (a) manufacturing a carbon substrate consisting essentially of a glass-like carbon and a crystalline carbon dispersed uniformly through said glass-like carbon, said manufacturing method comprising the steps of mixing crystalline carbon in a liquid composition of a thermosetting resin; molding said mixture into a desired substrate shape while performing control so that said crystalline carbon is uniformly dispersed therein; and baking said molding in an inert atmosphere or a non-oxidizing atmosphere or in a vacuum to obtain the carbon substrate,
   (b) making a cell adhere onto said carbon substrate;
   (c) causing said cell to proliferate on said carbon substrate; and
   (d) observing said cell adhered on the carbon substrate under a microscope by using reflected light.

2. A method of cell culture observation according to claim 1, wherein said cell is a neuron, said method further includes coating a surface of said carbon substrate with a substance for adsorbing said neuron thereon, and said cell proliferation includes allowing said neuron to extend along said neuron adsorbing substance applied as said coating.

3. A method of cell culture observation according to claim 2, wherein said neuron adsorbing substance is an extracellular matrix protein, a polyamino acid, or concanavalin A.

4. A method of cell culture observation according to claim 3, wherein said extracellular matrix protein is fibronectin, laminin, or collagen.

5. A method of cell culture observation according to claim 3, wherein said polyamino acid is poly-L lysine, poly-D lysine, or poly-D ornithine.

6. The carbon substrate for cell culture observation according to claim 1, wherein said carbon substrate contains crystalline carbon dispersed uniformly through said glass-like carbon, in proportions not smaller than 1% by mass but not larger than 40% by mass.

7. The carbon substrate for cell culture observation according to claim 1, wherein said crystalline carbon is at least one material selected from the group consisting of carbon nanotubes, graphite whiskers, highly oriented pyrolytic graphite, kish graphite, natural graphite, artificial graphite, fullerene, and graphite fiber chop.

8. The method of cell culture observation according to claim 1, wherein said baking includes heat-treating said molding at temperatures of 700° C. to 2800° C.

* * * * *